United States Patent [19]
Krüger et al.

[11] 4,093,734
[45] June 6, 1978

[54] AMINO-BENZOIC ACID AMIDES

[75] Inventors: Gerd Krüger; Johannes Keck, both of Biberach; Klaus Reinhold Noll, Warthausen; Helmut Pieper, Biberach; Harald Ziegler, Biberach; Helmut Ballhause, Biberach; Joachim Kähling, Biberach, all of Germany

[73] Assignee: Boehringer Ingelheim GmbH, Ingelheim am Rhein, Germany

[21] Appl. No.: 734,818

[22] Filed: Oct. 22, 1976

[30] Foreign Application Priority Data

Nov. 3, 1975  Germany ............................. 2548968
Aug. 10, 1976  Germany ............................. 2635873
Sep. 3, 1976  Germany ............................. 2639645

[51] Int. Cl.² .................... A61K 31/40; C07D 207/44
[52] U.S. Cl. .................... 424/274; 260/293.77; 260/293.53; 260/558 A; 544/165; 544/167; 548/320
[58] Field of Search ......... 260/326.47, 558 A, 293.77, 260/247.2 A, 295 AM; 424/274

[56] References Cited

U.S. PATENT DOCUMENTS

| 3,455,940 | 7/1969 | Stecker | 260/326.47 |
| 3,821,248 | 6/1974 | Griot | 260/326.47 |
| 3,891,671 | 6/1975 | Thominet | 260/326.47 |
| 3,900,481 | 8/1975 | Banitt et al. | 260/326.47 |
| 3,923,829 | 12/1975 | Denzler | 260/326.47 |
| 3,975,434 | 8/1976 | Buteau et al. | 260/326.47 |

OTHER PUBLICATIONS

Masuo et al., Chemical Abstracts, vol. 76, p. 72272g, (1972).
Duncan et al., Chemical Abstracts, vol. 80, 27095y, (1974).

Primary Examiner—Jose Tovar
Attorney, Agent, or Firm—Hammond & Littell

[57] ABSTRACT

Compounds of the formula

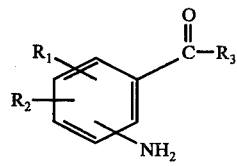

wherein
(a) when the amino-substituent is in the p-position with respect to the carbonyl group,
$R_1$ is chlorine in the o-position with respect to the carbonyl group,
$R_2$ is hydrogen, and
$R_3$ is ethylamino, cyclopentylamino, cyclohexylamino, cycloheptylamino, N-methyl-cyclohexylamino, benzylamino or 1-ethyl-pyrrolidyl-(2)-aminomethyl, or
(b) when the amino-substituent is in the o—, m— or p-position with respect to the carbonyl group,
$R_1$ is hydrogen, chlorine or bromine,
$R_2$ is trifluoromethyl, nitro or, when $R_4$ is 1-(alkyl of 1 to 3 carbon atoms)-pyrrolidyl or 1-(alkyl of 1 to 3 carbon atoms)-piperidyl, also fluorine, chlorine, bromine or methyl,
$R_3$ is (alkyl of 1 to 5 carbon atoms)-amino, (cycloalkyl of 3 to 7 carbon atoms)-amino, benzylamino, quinuclidinyl-amino or —NH—$(CH_2)_n$—$R_4$
where $R_4$ is pyridyl, 1-(alkyl of 1 to 3 carbon atoms)-pyrrolidyl, 1-(alkyl of 1 to 3 carbon atoms)-piperidyl or, when $n$ is 2 or 3, also imidazolonyl, pyrrolidino, piperidino or morpholino, and
$n$ is 0, 1, 2 or 3, and non-toxic, pharmacologically acceptable acid addition salts thereof; the compounds as well as their salts are useful as anxiolytics, anticonvulsives, antiemetics and antiulcerogenics.

7 Claims, No Drawings

AMINO-BENZOIC ACID AMIDES

This invention relates to novel amino-benzoic acid amides and non-toxic acid addition salts thereof, as well as to various methods of preparing these compounds.

THE PRIOR ART

German Offenlegungsschrift No. 1,795,723 discloses certain benzamides having psycho-pharmacologic and antiemetic properties, and it is stated that these properties are predicated upon the presence of a lower alkoxy substituent in o-position with respect to the amide group.

THE INVENTION

More particularly, the present invention relates to a novel class of amino-benzoic acid amides represented by the formula

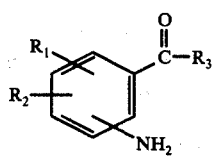

wherein
(a) when the amino-substituent is in the p-position with respect to the carbonyl group,
  $R_1$ is chlorine in the o-position with respect to the carbonyl group,
  $R_2$ is hydrogen, and
  $R_3$ is ethylamino, cyclopentylamino, cyclohexylamino, cycloheptylamino, N-methyl-cyclohexylamino, benzylamino or 1-ethyl-pyrrolidyl-(2)-aminomethyl, or
(b) when the amino-substituent is in the o—, m— or p-position with respect to the carbonyl group,
  $R_1$ is hydrogen, chlorine or bromine,
  $R_2$ is trifluoromethyl, nitro or, when $R_4$ is 1-(alkyl of 1 to 3 carbon atoms)-pyrrolidyl or 1-(alkyl of 1 to 3 carbon atoms)-piperidyl, also fluorine, chlorine, bromine or methyl,
  $R_3$ is (alkyl of 1 to 5 carbon atoms)-amino, (cycloalkyl of 3 to 7 carbon atoms)-amino, benzylamino, quinuclidinyl-amino or —NH—$(CH_2)_n$—$R_4$
    where $R_4$ is pyridyl, 1-(alkyl of 1 to 3 carbon atoms)-pyrrolidyl, 1-(alkyl of 1 to 3 carbon atoms)-piperidyl or, when $n$ is 2 or 3, also imidazolonyl, pyrrolidino, piperidino or morpholino, and
  $n$ is 0, 1, 2 or 3,
and non-toxic, pharmacologically acceptable acid addition salts thereof.

Specific preferred examples of the alkyl and cycloalkyl moieties of the variants of $R_3$ defined under (b) above are methyl, ethyl, isopropyl, n-butyl, tert.butyl, cyclopropyl, cyclobutyl, cyclopentyl, cyclohexyl and cycloheptyl, and preferred examples of the alkyl moieties of the variants of $R_4$ are methyl, ethyl, propyl and isopropyl.

An especially preferred subgenus of the present invention is constituted by compounds of the formula I, wherein
(a) the amino-substituent is in the p-position with respect to the carbonyl-substituent, $R_1$ is chlorine in the o-position with respect to the carbonyl-substituent, and
  $R_3$ is cyclohexylamino, N-methyl-cyclohexylamino or benzylamino, or
(b) the amino-substituent is in the o- or p-position with respect to the carbonyl-substituent,
  $R_1$ is hydrogen, chlorine or bromine,
  $R_2$ is trifluoromethyl, nitro or, when $R_4$ is 1-(alkyl of 1 to 3 carbon atoms)-pyrrolidyl, also methyl, fluorine, chlorine or bromine, and
  $R_3$ is —NH—$CH_2$—$R_4$, where $R_4$ is 1-(alkyl of 1 to 3 carbon atoms)-pyrrolidyl,
and non-toxic, pharmacologically acceptable acid addition salts thereof.

The compounds embraced by formula I may be prepared by the following methods:

METHOD A

By reacting an amino-benzoic acid of the formula

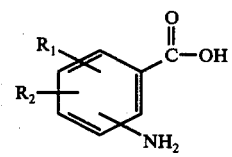

wherein $R_1$ and $R_2$ have the same meanings as in formula I, or a functional derivative thereof, with an amine of the formula $$H — R_3 \qquad (III)$$

wherein $R_3$ has the same meanings as in formula I, or also with a functional derivative thereof if a free carboxylic acid of the formula II is used.

Thus, the reaction may be carried out by reacting a carboxylic acid of the formula II or a functional derivative thereof with an amine of the formula III, optionally in the presence of an acid-activating and/or dehydrating agent, or by reacting a carboxylic acid of the formula II with a functional derivative of an amine of the formula III.

Examples of functional derivatives of a carboxylic acid of the formula II are their alkyl, aryl or aralkyl esters, such as the methyl, ethyl, phenyl or benzyl ester; their 1-imidazolyl-derivatives; their acid halides, such as the acid chlorides, acid bromides or acid iodides; their anhydrides; their mixed anhydrides with aliphatic or aromatic carboxylic acids, such as acetic acid or propionic acid or with carbonic esters, such as the ethyl ester; their acyloxytriphenyl-phosphonium salts; their N-acyloxy-imides; or, if the amino group is in the o-position on the phenyl ring, also their isatoic acid anhydrides of the formula

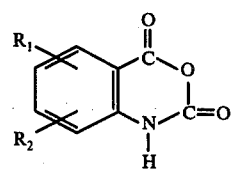

wherein $R_1$ and $R_2$ have the same meanings as in formula I.

Examples of functional derivatives of an amine of the formula III are their phosphazo-derivatives of the formula $$R_{x5}-NH-P=N-R_5 \quad (IIIa)$$

wherein $R_5$ is alkyl of 1 to 5 carbon atoms, cycloalkyl of 3 to 7 carbon atoms, benzyl or $$-(CH_2)_n-R_4,$$

wherein $R_4$ and $n$ have the same meanings as in formula I.

Examples of suitable dehydrating and/or acid-activating agents are chloroformic acid ester, such as ethyl chloroformate, thionyl chloride, phosphorus trichloride, phosphorus pentoxide, N,N'-dicyclohexyl-carbodiimide, N,N'-carbonyl-diimidazole, N,N'-thionyl-diimidazole and boron trifluoride etherate.

The reaction is advantageously carried out in the presence of a solvent, such as chloroform, carbon tetrachloride, ether, dioxane, tetrahydrofuran, benzene, toluene, dimethylformamide, methanol or an excess of the amine of the formula III, optionally in the presence of an inorganic base, such as sodium carbonate, or of a tertiary organic base, such as triethylamine or pyridine, which may at the same time serve as solvents, and optionally in the presence of an acid-activating agent, at temperatures between 0° and 250° C, preferably, however, at temperatures between 0° C and the boiling point of the particular solvent which is used. A functional derivative of a compound of the formula II or III which may be formed in situ need not be isolated. Furthermore, the reaction may also be carried out in the absence of a solvent and/or in the presence of a reaction accelerator, such as ammonium chloride. Finally, water formed during the reaction may be separated by azeotropic distillation, for example by heating with toluene in a vessel equipped with a water trap, optionally in the presence of a drying agent, such as magnesium sulfate.

METHOD B

For the preparation of a compound of the formula I wherein $R_1$ and/or $R_2$ are chlorine or bromine in the ortho- and/or para-position with respect to the amino-substituent, by halogenating an amino-benzoic acid derivative of the formula

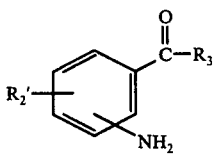
(IV)

wherein $R_3$ has the same meanings as in formula I, and $R_2'$ is hydrogen or has the same meanings as $R_2$ in formula I, or an acid addition salt thereof.

The reaction is carried out with a halogenating agent, such as with chlorine, bromine, sulfuryl chloride or bromine tribromophenolate, preferably in the presence of a solvent, such as 50% to 100% acetic acid, chloroform or methylene chloride; or with phenyl iodine dichloride in tetrahydrofuran and in the presence of a tertiary organic base, such as triethylamine or pyridine, and advantageously at temperatures between −20° and 50° C. Per mol of a compound of the formula IV, which may be used as a base or as a salt, for instance as a mono- or dihydrochloride, 1 mol or 2 mols of the halogenating or also an excess thereof up to 10 mols are employed.

METHOD C

For the preparation of an amino-benzoic acid amide of the formula I wherein $R_2$ is other than nitro, by reducing a nitro-benzoic acid amide of the formula

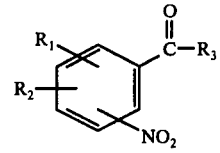
(V)

wherein $R_1$, $R_2$ and $R_3$ have the same meanings as in formula I.

The reduction is advantageously carried out in the presence of a solvent, such as water, methanol, ethanol, water/methanol or ethyl acetate, preferably with nascent hydrogen, for example generated with zinc/glacial acetic acid or iron-hydrochloric acid; or with hydrogen in the presence of a hydrogenation catalyst, such as Raney nickel, platinum or palladium/coal; or with hydrazine hydrate/Raney nickel; or with sodium dithionite or with tin(II)chloride/hydrochloric acid, at temperatures between 0° to 100° C, preferably, however, at temperatures between 10° and 80° C. If $R_2$ in a compound of the formula V is trifluoromethyl, the reduction is preferably carried out with nascent hydrogen or hydrazine hydrate/Raney nickel.

METHOD D

For the preparation of an amino-benzoic acid amide of the formula I wherein $R_2$ is other than nitro and $R_4$ is 1-(alkyl of 1 to 3 carbon atoms)-piperidyl, by alkylating a pyridine derivative of the formula

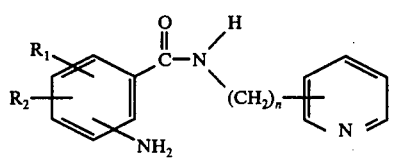
(VI)

wherein $R_1$, $R_2$ and $n$ have the same meanings as in formula I, followed by reduction of the obtained pyridinium salt with catalytically activated hydrogen.

The alkylation is carried out with an alkyl halide, such as methyl iodide or ethyl bromide, or a dialkyl sulfate, such as dimethyl sulfate, preferably in a solvent, such a ethanol, acetone, dimethyl sulfoxide, nitromethane, acetonitrile or dimethyl formamide, at temperatures between 0° and 150° C, but preferably at temperatures between 20° and 110° C. The subsequent catalytic hydrogenation of the obtained pyridinium salt is carried out in the presence of a solvent, such as methanol, ethanol, ethanol/water or water, with hydrogen in the presence of a hydrogenation catalyst such as Raney nickel, platinum or palladium/coal, at temperatures between 0° and 50° C, but preferably at room temperature.

METHOD E

By splitting off one or two protective substituents from the compound of the formula

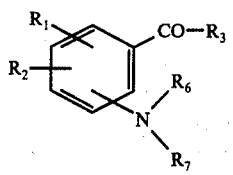

(VII)

wherein $R_1$, $R_2$ and $R_3$ have the same meanings as in formula I, $R_6$ is hydrogen or a protective substituent for an amino group, and $R_7$ is a protective substituent for an amino group or, together with $R_6$, phthaloyl.

Examples of protective substituents $R_6$ and $R_7$ are especially substituents which may easily be split off, such as the acetyl, propionyl, phthaloyl or trimethylsilyl.

The removal of the protective substituent is preferably effected in the presence of an acid, such as hydrochloric acid or sulfuric acid, in a solvent, such as water, dioxane/water, isopropanol or butanol, and at temperatures between 80° and 120° C, but preferably at the boiling point of the particular solvent which is used. It is of special advantage if the acid which is used, for instance, 6 N hydrochloric acid, can at the same time serve as a solvent.

The compounds embraced by formula I are organic bases and therefore form acid addition salts with 1 or 2 molar equivalents of an inorganic or organic acid. Examples of non-toxic, pharmacologically acceptable acid addition salts are those formed with hydrochloric acid, hydrobromic acid, sulfuric acid, phosphoric acid, lactic acid, citric acid, tartaric acid, maleic acid, fumaric acid, 8-chlorotheophylline or the like.

The starting compounds of the formulas II through VII are known compounds or may be obtained by known methods. For example, a compound of formula IV, V or VII is obtained by reacting a corresponding carboxylic acid with an acid-activating agent, followed by reaction of the intermediate with a corresponding amine.

The starting compounds of the formula VI for method D are obtained by any one of methods A – C and E.

The following examples illustrate the present invention and will enable others skilled in the art to understand it more completely. It should be understood, however, that the invention is not limited solely to the particular examples given below.

EXAMPLE 1

N-[1-Ethyl-pyrrolidyl-(2)-methyl]-2-amino-5-chloro-3-trifluoro-methyl-benzoic acid amide and its hydrochloride by method A A solution of 70.0 gm of 2-amino-5-chloro-3-trifluoromethyl-benzoic acid chloride in 600 ml of chloroform was added over a period of half an hour to a solution of 46.2 ml of triethylamine and 38.5 gm of 1-ethyl-2-amino-methyl-pyrrolidine in 200 ml of chloroform, while stirring and cooling with water (warming to 30° C). 15 minutes after completion of the addition the reaction solution was washed twice with 300 ml of 2 N ammonia and once with 500 ml of water. The organic phase was dried with magnesium sulfate, and the solvent was distilled off in vacuo. The crystalline, yellowish evaporation residue was purified by chromatography on silicagel (eluant: chloroform/methanol = 8/2). The eluate fractions containing the desired compound were combined and evaporated in vacuo, and the residue was dissolved in ether. Upon addition of ethereal hydrochloric acid to the ethereal solution of N-[1-ethyl-pyrrolidyl-(2)-methyl]-2-amino-5-chloro-3-trifluoromethyl-benzoic acid amide, a precipitate formed which was suction-filtered off and recrystallized from isopropanol, whereupon it had a melting point of 192°–194° C (decomp.). It was identified to be the hydrochloride of the formula

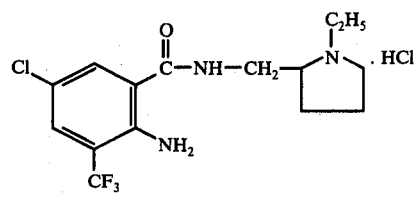

EXAMPLE 2

N-[1-Ethyl-pyrrolidyl-(2)-methyl]-2-amino-3-chloro-5-nitrobenzoic acid amide by method B 7.5 gm of N-[1-ethyl-pyrrolidyl-(2)-methyl]-2-amino-5-nitro-benzoic acid amide were dissolved in 200 ml of 95% acetic acid, and a solution of 1.8 gm of chlorine in 30 ml of 95% acetic acid was added at 7° C. One minute later the reaction mixture was poured into 500 gm of ice water. The mixture was made alkaline with ammonia, extracted with chloroform, and the chloroform extract was evaporated to dryness. N-[1-ethyl-pyrrolidyl-(2)-methyl]-2-amino-3-chloro-5-nitrobenzoic acid amide, m.p. 157°–160° C, was obtained by crystallization of the residue from ethanol.

EXAMPLE 3

N-[1-Ethyl-pyrrolidyl-(2)-methyl]-2-amino-5-bromo-3-trifluoromethyl-benzoic acid amide A solution of 0.82 ml of bromine in 20 ml of glacial acetic acid was added dropwise over a period of 15 minutes to a solution of 5.0 gm of N-[1-ethyl-pyrrolidyl-(2)-methyl]-2-amino-3-trifluoromethyl-benzoic acid amide in 75 ml of 67% acetic acid at about 20° C. The resulting mixture was stirred for 1 hour at the same temperature, and then the solvents were distilled off in vacuo. The residue was distributed between ethyl acetate and an aqueous 10% sodium carbonate solution. The organic phase was washed with water, dried with magnesium sulfate and again evaporated in vacuo. The residual product was purified by column chromatography (silicagel; methanol). The fractions containing the desired product were combined and concentrated in vacuo. The residual oil was dissolved in ether, and after addition of ethereal hydrochloric acid, N-[1-ethyl-pyrrolidyl-(2)-methyl]-2-amino-5-bromo-3-trifluoromethyl-benzoic acid amide hydrochloride crystallized out, which was isolated and recrystallized from isopropanol; m.p. 210°–213° C.

EXAMPLE 14

N-[1-Ethyl-pyrrolidyl-(2)-methyl]-2-amino-5-methyl-benzoic acid amide by method C 69 gm of N-[1-ethyl-pyrrolidyl-(2)-methyl]-5-methyl-2-nitro-benzoic acid amide were dissolved in 900 ml of methanol, and the solution was hydrogenated in the presence of 15 gm of Raney nickel at room temperature and 50 atmospheres pressure. After the hydrogen absorption was finished, a small quantity of charcoal was added, and the mixture was filtered. The filtrate was concentrated by evaporation, and upon cooling N-[1-ethyl-pyrrolidyl-(2)-methyl]-2-amino-5-methyl-benzoic acid amide, m.p. 81°–85° C, crystallized out. The dihydrochloride, m.p. 170°–175° C, was obtained from the solution of the base in ethanol by addition of isopropanolic hydrochloric acid.

EXAMPLE 5

N-[1-Ethyl-piperidyl-(3)-methyl]-2-amino-5-chloro-3-trifluoro -methyl-benzoic acid amide by method D 3.6 gm of 2-amino-5-chloro-N-[pyridyl-(3)-methyl]-3-trifluoromethyl-benzoic acid amide in 100 ml of dimethylformamide were admixed with 1.6 ml of ethyl iodide, and the mixture was heated on a steam bath for 9 hours. Then the mixture was evaporated in vacuo, and the obtained oily 1-ethyl- 3-[N-(2-amino-5-chloro-3-trifluoromethyl-benzoyl)-amino-methyl]-pyridinium iodide was purified by column chromatography (silicagel; chloroform/methanol = 8/2). The residue (4.9 gm) obtained after evaporation in vacuo of the fractions containing the desired product was dissolved in 50 ml of absolute methanol and treated with hydrogen in a Parr-apparatus in the presence of 1.5 gm of platinum dioxide (20° C, 1 atmosphere). After the hydrogen absorption had gone to completion, the catalyst was filtered off, and the filtrate was evaporated in vacuo. The evaporation residue was dissolved in chloroform, and the solution was washed first with an aqueous 10% sodium bisulfite solution and then with 2 N ammonia. The organic phase was dried with magnesium sulfate and evaporated in vacuo. The residue was triturated with water and the product, N-[1-ethyl-piperidyl-(3)-methyl]-2-amino-5-chloro-3-trifluoromethyl-benzoic acid amide, m.p. 114°–117° C, was collected by suction filtration.

EXAMPLE 6

4-Amino-2-chloro-N-cyclohexyl-N-methyl-benzoic acid amide by method A

A mixture of 15 gm of N-(4-amino-2-chloro-benzoyl)-imidazole (m.p. 122°–127° C) and 150 ml of N-methyl-cyclohexylamine was stirred at 130° C for 4 hours. Subsequently, chloroform was added to the reaction mixture, and the resulting mixture was extracted twice with 300 ml of water. The organic phase was dried with sodium sulfate and evaporated. The oily residue was purified by chromatography on a silicagel column with chloroform/methanol (6:1), and the combined eluate fractions containing the desired product were evaporated. The residue was crystallized from isopropanol, yielding 4-amino-2-chloro-N-cyclohexyl-N-methyl-benzoic acid amide, m.p. 166°–170° C.

EXAMPLE 7

N-[1-Ethyl-pyrrolidyl-(2)-methyl]-2-amino-3-chloro-benzoic acid amide by method A (a) 468 gm of N-ethoxycarbonyl-3-chloro-anthranilic acid (m.p. 111°–114° C) were refluxed in 1500 ml of dioxane with 420 ml of thionyl chloride for 3 hours while stirring. Thereafter, the reaction solution was evaporated in vacuo until crystallization started, and then cooled. The precipitate was collected by suction filtration and washed with ether. 8-Chloro-2H-3,1-benzoxazine-2,4(1H)-dione, m.p. 225°–230° C, was obtained.

(b) 59.3 gm of 8-chloro-2H-3,1-benzoxazine-2,4(1H)-dione were suspended in 400 ml of tetrahydrofuran, and a solution of 38.6 gm of 1-ethyl-2-aminomethyl-pyrrolidine in 150 ml of tetrahydrofuran was added dropwise while stirring and cooling (ice water). The resulting mixture was allowed to stand for 30 minutes on an ice water bath, and was then evaporated to dryness in vacuo. The residue was taken up in 300 ml of dichloromethane, the solution was filtered, and the filtrate was extracted with 2 N hydrochloric acid. The acidic extract was made alkaline with concentrated ammonia and was then extracted with ether. The ether phase was washed with water, dried (magnesium sulfate) and evaporated in vacuo. The oily residue of N-[1-ethyl-pyrrolidyl-(2)-methyl]-2-amino-3-chloro -benzoic acid amide was crystallized from 500 ml of n-hexane/ether (10:1), suction-filtered and recrystallized from ether and n-hexane; m.p. 78°–80° C.

EXAMPLE 8

N-[1-Ethyl-piperidyl-(3)]-2-amino-5-bromo-3-trifluoromethyl-benzoic acid amide, m.p. 145°–147° C, was prepared from 2-amino-5-bromo-3-trifluoromethyl-benzoic acid chloride and 1-ethyl-3-amino-piperidine analogous to Example 1.

EXAMPLE 9

4-Amino-3-chloro-N-(2-morpholino-ethyl)-5-trifluoromethyl-benzoic acid amide, m.p. 138°–141° C (decomp.), was prepared from 4-amino-3-chloro-5-trifluoromethyl-benzoic acid chloride and 2-morpholino-ethylamine analogous to Example 1.

EXAMPLE 10

N-[1-Ethyl-piperidyl-(3)]-4-amino-3-chloro-5-trifluoromethyl-benzoic acid amide (m.p. of its hydrochloride: 221°–223° C), was prepared from 4-amino-3-chloro-5-trifluoromethyl-benzoic acid chloride and 1-ethyl-3-amino-piperidine analogous to Example 1.

EXAMPLE 11

4-Amino-3-chloro-N-(2-piperidino-ethyl)-5-trifluoromethyl-benzoic acid amide, m.p. 105°–107° C, was prepared from 4-amino-3-chloro-5-trifluoromethyl-benzoic acid chloride and 2-piperidino-ethylamine analogous to Example 1.

EXAMPLE 12

4-Amino-3-chloro-N-(2-pyrrolidino-ethyl)-5-trifluoromethyl-benzoic acid amide, m.p. 134.5°–136.5° C, was prepared from 4-amino-3-chloro-5-trifluoromethyl-benzoic acid chloride and 2-pyrrolidino-ethylamine analogous to Example 1.

EXAMPLE 13

4-Amino-3-chloro-N-(3-morpholino-propyl)-5-trifluoromethyl-benzoic acid amide [m.p. of its hydrochloride: 173–178° C (decomp.)], was prepared from 4-amino-3-chloro-5-trifluoromethyl-benzoic acid chloride and 3-morpholino-propylamine analogous to Example 1.

EXAMPLE 14

N-[1-Ethyl-piperidyl-(3)]-2-amino-5-chloro-3-trifluoromethyl-benzoic acid amide, m.p. 138°–141° C, was prepared from 2-amino-5-chloro-3-trifluoromethylbenzoic acid chloride and 1-ethyl-3-amino-piperidine analogous to Example 1.

EXAMPLE 15

2-Amino-5-chloro-N-(2-pyrrolidino-ethyl)-3-trifluoromethyl-benzoic acid amide, m.p. 116°–118° C, was prepared from 2-amino-5-chloro-3-trifluoromethyl-benzoic acid chloride and 2-pyrrolidino-ethylamine analogous to Example 1.

EXAMPLE 16

4-Amino-3-chloro-N-[2-(2-oxo-imidazolidino)-ethyl]-5-trifluoromethyl-benzoic acid amide, m.p. 172°–174° C, was prepared from 4-amino-3-chloro-5-trifluoromethyl-benzoic acid chloride and 2-(2-oxo-imidazolidino)-ethylamine analogous to Example 1.

EXAMPLE 17

4-Amino-3-chloro-N-[pyridyl-(4)-methyl]-5-trifluoromethyl-benzoic acid amide, m.p. 158°–160° C, was prepared from 4-amino-3-chloro-5-trifluoromethyl-benzoic acid chloride and 4-aminomethyl-pyridine analogous to Example 1.

EXAMPLE 18

2-Amino-5-chloro-N-(2-piperidino-ethyl)-3-trifluoromethyl-benzoic acid amide, m.p. 109°–111° C, was prepared from 2-amino-5-chloro-3-trifluoromethyl-benzoic acid chloride and 2-piperidino-ethylamine analogous to Example 1.

EXAMPLE 19

2-Amino-5-chloro-N-[pyridyl-(2)-methyl]-3-trifluoromethyl-benzoic acid amide, m.p. 127°–129° C, was prepared from 2-amino-5-chloro-3-trifluoromethyl-benzoic acid chloride and 2-aminomethyl-pyridine analogous to Example 1.

EXAMPLE 20

2-Amino-5-chloro-N-(2-morpholino-ethyl)-3-trifluoromethyl-benzoic acid amide, m.p. 133°–135° C, was prepared from 2-amino-5-chloro-3-trifluoromethyl-benzoic acid chloride and 2-morpholino-ethylamine analogous to Example 1.

EXAMPLE 21

2-Amino-5-chloro-N-(3-morpholino-propyl)-3-trifluoromethyl-benzoic acid amide, m.p. 107°–110° C]m.p. of its hydrochloride: 237°–241° C (decomp.)], was prepared from 2-amino-5-chloro-3-trifluoromethyl-benzoic acid chloride and 3-morpholino-propylamine analogous to Example 1.

EXAMPLE 22

N-[1-Ethyl-pyrrolidyl-(2)-methyl]-2-amino-3,5-dibromo-benzoic acid amide (m.p. of its hydrochloride: 227°–231° C), was prepared from 2-amino-3,5-dibromo-benzoic acid chloride and 1-ethyl-2-aminomethyl-pyrrolidine analogous to Example 1.

EXAMPLE 23

N-[1-Ethyl-pyrrolidyl-(2)-methyl]-2-amino-3,5-dichloro-benzoic acid amide (m.p. of its hydrochloride: 190°–192° C), was prepared from 2-amino-3,5-dichloro-benzoic acid chloride and 1-ethyl-2-aminomethyl-pyrrolidine analogous to Example 1.

EXAMPLE 24

N-[1-Ethyl-pyrrolidyl-(2)-methyl]-4-amino-3-bromo-5-fluoro-benzoic acid amide (m.p. of its hydrochloride: 164°–166° C), was prepared from 4-amino-3-bromo-5-fluoro-benzoic acid chloride and 1-ethyl-2-aminomethyl-pyrrolidine analogous to Example 1.

EXAMPLE 25

N-[1-Ethyl-pyrrolidyl-(2)-methyl]-4-amino-3-chloro-5-fluoro-benzoic acid amide, m.p. 102°–104° C, was prepared from 4-amino-3-chloro-5-fluoro-benzoic acid chloride and 1-ethyl-2-aminomethyl-pyrrolidine analogous to Example 1.

EXAMPLE 26

N-[1-Ethyl-pyrrolidyl-(2)-methyl]-4-amino-3-chloro-5-trifluoromethyl-benzoic acid amide (m.p. of its hydrochloride: 170°–173° C), was prepared from 4-amino-3-chloro-5-trifluoromethyl-benzoic acid chloride and 1-ethyl-2-aminomethyl-pyrrolidine analogous to Example 1.

EXAMPLE 27

2-Amino-5-bromo-N-[pyridyl-(2)-methyl]-3-trifluoromethyl-benzoic acid amide, m.p. 126°–128° C, was prepared from 2-amino-5-bromo-3-trifluoromethyl-benzoic acid chloride and 2-aminomethyl-pyridine analogous to Example 1.

EXAMPLE 28

N-[1-Ethyl-pyrrolidyl-(2)-methyl]-4-amino-3-bromo-5-trifluoromethyl-benzoic acid amide (m.p. of its hydrochloride: 184°–186° C), was prepared from 4-amino-3-bromo-5-trifluoromethyl-benzoic acid chloride and 1-ethyl-2-aminomethyl-pyrrolidine analogous to Example 1.

EXAMPLE 29

4-Amino-3-chloro-N-[pyridyl-(3)]-5-trifluoromethyl-benzoic acid amide [m.p. of its hydrochloride: 244°–249° C (decomp.)], was prepared from 4-amino-3-chloro-5-trifluoromethyl-benzoic acid chloride and 3-amino-pyridine analogous to Example 1.

EXAMPLE 30

4-Amino-N-[quinuclidinyl-(3)]-3-chloro-5-trifluoromethyl-benzoic acid amide, m.p. 233°–236° C, was prepared from 4-amino-3-chloro-5-trifluoromethyl-benzoic acid chloride and 3-amino-quinuclidine analogous to Example 1.

EXAMPLE 31

4-Amino-3-chloro-N-[pyridyl-(4)]-5-trifluoromethyl-benzoic acid amide, m.p. 191°–193° C, was prepared from 4-amino-3-chloro-5-trifluoromethyl-benzoic acid chloride and 4-amino-pyridine analogous to Example 1.

EXAMPLE 32

2-Amino-5-chloro-N-[pyridyl-(3)-methyl]-3-trifluoromethyl-benzoic acid amide, m.p. 128°–129° C (decomp.), was prepared from 2-amino-5-chloro-3-trifluoromethyl-benzoic acid chloride and 3-aminomethyl-pyridine analogous to Example 1.

EXAMPLE 33

4-Amino-N-tert.butyl-3-chloro-5-trifluoromethyl-benzoic acid amide, m.p. 144°–145° C, was prepared from 4-amino-3-chloro-5-trifluoromethyl-benzoic acid chloride and tert.butylamine analogous to Example 1.

EXAMPLE 34

4-Amino-3-chloro-N-cyclopropyl-5-trifluoromethyl-benzoic acid amide, m.p. 126°–127° C, was prepared from 4-amino-3-chloro-5-trifluoromethyl-benzoic acid chloride and cyclopropylamine analogous to Example 1.

EXAMPLE 35

4-Amino-N-(n-butyl)-3-chloro-5-trifluoromethyl-benzoic acid amide, m.p. 94°–96° C, was prepared from 4-amino-3-chloro-5-trifluoromethyl-benzoic acid chloride and n-butylamine analogous to Example 1.

EXAMPLE 36

4-Amino-N-benzyl-3-chloro-5-trifluoromethyl-benzoic acid amide, m.p. 134°–135° C, was prepared from 4-amino-3-chloro-5-trifluoromethyl-benzoic acid chloride and benzylamine analogous to Example 1.

EXAMPLE 37

N-[1-Ethyl-pyrrolidyl - (2)-methyl]-4-amino-3,5-dichloro-benzoic acid amide, m.p. 98°–100° C, was prepared from 4-amino-3,5-dichloro-benzoic acid chloride and 1-ethyl-2-aminomethyl-pyrrolidine analogous to Example 1.

EXAMPLE 38

N-[1-Ethyl-pyrrolidyl-(2)-methyl]-4-amino-3,5-dibromo-benzoic acid amide (m.p. of its hydrochloride: 177°–178° C), was prepared from 4-amino-3,5-dibromo-benzoic acid chloride and 1-ethyl-2-aminomethyl-pyrrolidine analogous to Example 1.

EXAMPLE 39

N-[1-Ethyl-pyrrolidyl-(2)-methyl]-2-amino-3-bromo-5-chloro-benzoic acid amide (m.p. of the hydrochloride: 216°–217° C), was prepared from 2-amino-3-bromo-5-chloro-benzoic acid chloride and 1-ethyl-2-aminomethyl-pyrrolidine analogous to Example 1.

EXAMPLE 40

N-[1-Ethyl-pyrrolidyl-(2)-methyl]-3-amino-2,5-dichloro-benzoic acid amide (m.p. of its hydrochloride: 204°–205.5° C), was prepared from 3-amino-2,5-dichloro-benzoic acid chloride and 1-ethyl-2-aminomethyl-pyrrolidine analogous to Example 1.

EXAMPLE 41

N-[1-Ethyl-pyrrolidyl-(2)-methyl]-2-amino-3-bromo-5-fluoro-benzoic acid amide, m.p. 100°–101° C, was prepared from 2-amino-3-bromo-5-fluoro-benzoic acid chloride and 1-ethyl-2-aminomethyl-pyrrolidine analogous to Example 1.

EXAMPLE 42

2-Amino-N-[pyridyl-(3)-methyl]-3-trifluoromethyl-benzoic acid amide, m.p. 113°–114° C, was prepared from 2-amino-3-trifluoromethyl-benzoic acid chloride and 3-aminomethyl-pyrridine analogous to Example 1.

EXAMPLE 43

N-[1-Ethyl-pyrrolidyl-(2)-methyl]-4-amino-2-chloro-benzoic acid amide (m.p. of its hydrochloride: 199°–203° C), was prepared from 4-amino-2-chloro-benzoic acid chloride and 1-ethyl-2-aminomethyl-pyrrolidine analogous to Example 1.

EXAMPLE 44

N-[1-Ethyl-pyrrolidyl-(2)-methyl]-2-amino-5-bromo-3-chloro-benzoic acid amide (m.p. of its hydrochloride: 210°–212° C), was prepared from 2-amino-5-bromo-3-chloro-benzoic acid chloride and 1-ethyl-2-aminomethyl-pyrrolidine analogous to Example 1.

EXAMPLE 45

4-Amino-2-chloro-N-cyclohexyl-benzoic acid amide (m.p. of its hydrochloride: 225°–229° C), was prepared from 4-amino-2-chloro-benzoic acid chloride and cyclohexylamine analogous to Example 1.

EXAMPLE 46

4-Amino-N-benzyl-2-chloro-benzoic acid amide (m.p. of its hydrochloride: 224.5°–225.5° C), was prepared from 4-amino-2-chloro-benzoic acid chloride and benzylamine analogous to Example 1.

EXAMPLE 47

N-Ethyl-4-amino-2-chloro-benzoic acid amide (m.p. of its hydrochloride: 216°–220° C), was prepared from 4-amino-2-chloro-benzoic acid chloride and ethylamine analogous to Example 1.

EXAMPLE 48

4-Amino-2-chloro-N-cyclopentyl-benzoic acid amide (m.p. of its hydrochloride 215°–217° C), was prepared from 4-amino-2-chloro-benzoic acid chloride and cyclopentyl-amine analogous to Example 1.

EXAMPLE 49

4-Amino-2-chloro-N-cycloheptyl-benzoic acid amide, m.p. 133.5°–135° C, was prepared from 4-amino-2-chloro-benzoic acid chloride and cycloheptyl-amine analogous to Example 1.

EXAMPLE 50

2-Amino-5-bromo-N-[pyridyl-(3)-methyl]-3-trifluoromethyl-benzoic acid amide, m.p. 135°–137° C, was prepared from 2-amino-5-bromo-3-trifluoromethyl-benzoic acid and 3-aminomethyl-pyridine analogous to Example 1.

EXAMPLE 51

N-[1-Ethyl-pyrrolidyl-(2)-methyl]-2-amino-3-chloro-5-methyl-benzoic acid amide, m.p. 87°–91° C, was prepared from 2-amino-3-chloro-5-methyl-benzoic acid chloride and 1-ethyl-2-aminomethyl-pyrrolidine analogous to Example 1.

EXAMPLE 52

N-[1-Ethyl-pyrrolidyl-(2)-methyl]-4-amino-3-chloro-5-nitro-benzoic acid amide (m.p. of its hydrochloride: above 120° C decomp.), was prepared from N-[1-ethyl-pyrrolidyl-(2)-methyl]-4-amino-5-nitro-benzoic acid amide and chlorine analogous to Example 2.

EXAMPLE 53

N-[1-Ethyl-pyrrolidyl-(2)-methyl]-2-amino-3-bromo-5-nitro-benzoic acid amide, m.p. 173°–177° C, was prepared from N-[1-ethyl-pyrrolidyl-(2)-methyl]-2-amino-5-nitro-benzoic acid amide and bromine analogous to Example 3.

EXAMPLE 54

N-[1-Ethyl-pyrrolidyl-(2)-methyl]-2-amino-3-bromo-5-methyl-benzoic acid amide, m.p. 102°–104° C (m.p. of its hydrochloride: 143°–149° C), was prepared from N-[1-ethyl-pyrrolidyl-(2)-methyl]-2-amino-5-methyl-benzoic acid amide and bromine analogous to Example 3.

EXAMPLE 55

N-[1-Ethyl-piperidyl-(2)-methyl]-4-amino-3-chloro-5-trifluoro-methyl-benzoic acid amide [m.p. of its hydrochloride: 212°–215° C (decomp.)], was prepared from 4-amino-3-chloro-N-[pyridyl-(2)-methyl]-5-trifluoromethyl-benzoic acid amide (m.p. 185°–187° C) and ethyl iodide with subsequent catalytic hydrogenation analogous to Example 5.

EXAMPLE 56

4-Amino-3-chloro-N-[1-methyl-piperidyl-(4)]-5-trifluoromethyl-benzoic acid amide, m.p. 193°–194° C, was prepared from 4-amino-3-chloro-N-[pyridyl-(4)]-5-trifluoromethyl-benzoic acid amide and methyl iodide with subsequent catalytic hydrogenation analogous to Example 5.

EXAMPLE 57

2-Amino-5-chloro-N-[1-methyl-pyrrolidyl-(2)-methyl]-3-trifluoromethyl-benzoic acid amide, m.p. 94°–96° C, was prepared from 2-amino-5-chloro-3-trifluoromethyl-benzoic acid chloride and 2-aminomethyl-1-methyl-pyrrolidine analogous to Example 1.

EXAMPLE 58

N-[1-Ethyl-pyrrolidyl-(2)-methyl]-2-amino-3-chloro-5-trifluoromethyl-benzoic acid amide (m.p. of its hydrochloride: 191°–193° C), was prepared from 2-amino-3-chloro-5-trifluoromethyl-benzoic acid chloride and 1-ethyl-2-aminomethyl-pyrrolidine analogous to Example 1.

The following compounds were also prepared analogous to Example 1:

N-[1-ethyl-pyrrolidyl-(2)-methyl]-2-amino-3-chloro-5-methyl-benzoic acid amide, m.p. 87°–91° C.
N-[1-ethyl-pyrrolidyl-(2)-methyl]-2-amino-3-chloro-5-nitro-benzoic acid amide, m.p. 157°–160° C.
N-[1-ethyl-pyrrolidyl-(2)-methyl]-4-amino-3-chloro-5-fluoro-benzoic acid amide, m.p. 102°–104° C.
N-[1-ethyl-pyrrolidyl-(2)-methyl]-2-amino-3,5-dichloro-benzoic acid amide hydrochloride, m.p. 190°–192° C.
N-[1-ethyl-pyrrolidyl-(2)-methyl]-2-amino-5-bromo-3-chloro-benzoic acid amide hydrochloride, m.p. 210°–212° C.
4-Amino-2-chloro-N-cyclohexyl-benzoic acid amide hydrochloride, m.p. 225°–229° C.
4-Amino-N-benzyl-2-chloro-benzoic acid amide hydrochloride, m.p. 224.5°–225.5° C.
4-Amino-2-chloro-N-cyclohexyl-N-methyl-benzoic acid amide, m.p. 166°–170° C.
N-[1-ethyl-pyrrolidyl-(2)-methyl]-4-amino-3-chloro-5-trifluoromethyl-benzoic acid amide hydrochloride, m.p. 170°–173° C.
2-Amino-5-chloro-N-[pyridyl-(3)-methyl]-3-trifluoromethyl-benzoic acid amide, m.p. 128°–129° C (decomp.).

The compounds of the present invention, that is, those embraced by formula I above and their non-toxic, pharmacologically acceptable acid addition salts, have useful pharmacodynamic properties. More particularly, they exhibit primarily anxiolytic (anxiety-relieving) and anticonvulsive activities besides antiemetic and antiulcerogenic activities with good oral absorption in warm-blood animals, such as mice and rats.

The anxiolytic and anticonvulsive properties of the compounds of this invention were ascertained by the standard pharmacological test methods described below, and the tables show the results obtained for a few representative compounds, where A = N-[1-ethyl-pyrrolidyl-(2)-methyl]-2-amino-3-chloro-5-methyl-benzoic acid amide,
B = N-[1-ethyl-pyrrolidyl-(2)-methyl]-2-amino-3-chloro-5-nitro-benzoic acid amide,
C = N-[1-ethyl-pyrrolidyl-(2)-methyl]-4-amino-3-chloro-5-fluoro-benzoic acid amide,
D = N-[1-ethyl-pyrrolidyl-(2)-methyl]-2-amino-3,5-dichlorobenzoic acid amide hydrochloride,
E = N-[1-ethyl-pyrrolidyl-(2)-methyl]-2-amino-5-bromo-3-chloro-benzoic acid amide hydrochloride,
F = 4-amino-2-chloro-N-cyclohexyl-benzoic acid amide hydrochloride,
G = 4-amino-N-benzyl-2-chloro-benzoic acid amide hydrochloride,
H = 4-amino-2-chloro-N-cyclohexyl-N-methyl-benzoic acid amide,
I = N-[1-ethyl-pyrrolidyl-(2)-methyl]-2-amino-5-chloro-3-trifluoromethyl-benzoic acid amide hydrochloride,
J = N-[1-ethyl-pyrrolidyl-(2)-methyl]-4-amino-3-chloro-5-trifluoromethyl-benzoic acid amide hydrochloride, and
K = 2-amino-5-chloro-N-[pyridyl-(3)-methyl]-3-trifluoromethyl-benzoic acid amide.

1. ANTICONVULSIVE ACTIVITY IN MICE

Method

Male mice with body weights between 20 and 26 gm were used as experimental animals. They were allowed free access to food (Altromin ®) and water up to one hour before administration of the test compound.

Tests were carried out by using the maximal electroshock seizure pattern [Swinyard, Brown and Goodman, J. Pharmacol. exp. Ther. 106, 319 (1952)].

The electroshock apparatus was constructed according to Woodbury and Davenport [Arch. int. Pharmacodyn. 99, 97 (1952)]. The electric impulses (50 Hz A.C., 50 mA, 0.2 sec) were delivered via steel ball electrodes covered with buckskin and moistened with 0.9% sodium chloride solution placed on the heads and over the eyes of the mice.

The test is a measure of the ability of anticonvulsive drugs to abolish the hindlimb tonic extensor component of the maximal seizure pattern induced by electric stimulation.

The test compound was administered either as the free base or as the hydrochloride. The free base was suspended in 1% tylose, and the hydrochloride was dissolved in distilled water. Each compound was administered orally to 10 animals/dose in a volume of 0.1 ml solution or suspension per 10 gm of mouse. Control groups received only the suspension agent or solvent orally. 30, 150 and 300 minutes after administration all animals were shocked. $ED_{50}$-values were determined graphically as a measure of the ability of the test compounds to abolish the hindlimb tonic extensor component of the maximal seizure pattern in 50 percent of animals

TABLE I

| Compound | $ED_{50}$ mgm/kg p.o. | | |
|---|---|---|---|
| | 30 | 150 | 300 min. |
| A | 28 | 60 | 102 |
| B | 78 | 130 | 178 |
| C | 37 | 50 | 128 |
| D | 35 | 54 | 109 |
| E | 44 | 68 | 109 |
| F | 38 | 50 | 116 |
| G | 68 | 133 | 200 |
| H | 200 | 155 | 200 |
| I | 72 | 100 | 124 |
| J | 62 | 64 | 82 |
| K | >200 | 70 | 73 |

2. ANXIOLYTIC ACTIVITY

Vogel, Beer and Clody [Psychopharmacologia 21, 1 (1971)] showed that the anxiety-relieving effect of psychoactive compounds can be tested on naive rats. In their experiments, the drinking frequency of thirsty animals served as a measure for anxiety-relieving effects.

METHOD

Female rats with body weights between 150 and 170 gm were used as experimental animals. Food was available at all times, whereas they were deprived of water for 48 hours prior to the test session.

The test apparatus was an opaque plastic box (24 × 24 × 22 cm), provided with a plexiglass cover and a stainlesssteel grid floor. The metal drinking tube of a 250 ml-bottle covered with a hard plastic projected 2 cm from the wall into the box, the tube being attached to one side at a height of 6.5 cm. A piece of 0.2 cm at the tip of the tube was not plastic-covered. An electrical circuit was connected between the tube and the grid floor. Whenever a rat closed the circuit by licking the tube, each lick was counted electronically. At every 20th lick the animal received an electro-shock (40 V, 10 mA A.C.) via the tube ending and the grid. After the first 20 licks a time-counter was switched on, finishing the test after 3 minutes. Within this period the drinking frequency of each animal was recorded as the number of shocks delivered during the 3-minute session.

The test compound was orally administered to 10 rats at a dosage level of 10 mgm/kg in aqueous solution or in a suspension of 1% tylose in a volume of 0.5 ml solution or suspension per 100 gm animal one hour before testing. The control groups received only the solvent or suspension agent.

Statistical comparisons were made, using the Mann-Whitney-U-test (Siegel: Nonparametric Statistics, McGraw-Hill, 1956).

TABLE II

| Compound | Shocks/animal | | |
|---|---|---|---|
| | Controls | Treated animals | Difference |
| A | 3.5 | 7.1 | + 3.6+ |
| B | 3.7 | 4.9 | + 1.2° |
| C | 2.8 | 6.7 | ° 3.9+ |
| D | 3.7 | 6.8 | + 3.1° |
| E | 3.0 | 7.5 | + 4.5° |
| F | 3.3 | 5.3 | + 2.0° |
| G | 3.3 | 7.1 | + 3.8 |
| H | 3.2 | 7.8 | + 4.6+ |
| I | 2.9 | 7.5 | + 4.6+ |
| J | 3.6 | 7.2 | + 3.6° |

TABLE II-continued

| Compound | Shocks/animal | | |
|---|---|---|---|
| | Controls | Treated animals | Difference |
| K | 3.5 | 9.6 | + 6.1+ |

+significant difference compared with control group, p >0.05
°difference compared with control group, p >0.1

3. ACUTE TOXICITY IN THE MOUSE AFTER INTRAVENOUS ADMINISTRATION

Method 5 female and 5 male mice per dose, with body weights between 20 and 26 gm, served as test animals. The animals had access to food and drinking water ad libitum.

Compounds D, E, I and J were dissolved in distilled water, compounds A, B and C in 0.2% tartaric acid, and compound G in 15% propylene glycol.

The injected volume at the dosage level of 50 mgm/kg i.v. amounted to 0.1 ml/10 gm of animal. When the dosage was increased or diminished by 10 mgm/kg i.v., the volume was increased or diminished by 0.04 ml, respectively. Control groups of 10 animals each were only treated with the solvent.

Subsequently, the mice were separated into groups of 5 animals according to sex and dosage and were observed in macrolon cages for 14 days.

The $LD_{50}$-values were determined according to the graphic-statistical method of Litchfield and Wilcoxon [(J. Pharmacol. exp. Therap. 96, 99, (1949)].

TABLE III

| Compound | $LD_{50}$ mgm/kg i.v. |
|---|---|
| A | 28.6 |
| B | 39 |
| C | 28.5 |
| D | 31.5 |
| E | 25 |
| G | 48 |
| I | 52.5 |
| J | 33.5 |

The following examples serve to illustrate the invention:

For pharmaceutical purposes the compounds according to the present invention are administered to warm-blooded animals perorally or parenterally as active ingredients in customary dosage unit compositions, that is, compositions in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.16 to 0.84 mgm/kg body weight.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 59

Tablets

The tablet composition is compounded from the following ingredients:

N-[1-Ethyl-pyrrolidyl-(2)-methyl]-2-

-continued

| | |
|---|---|
| amino-5-chloro-3-trifluoromethyl-benzoic acid amide hydrochloride | 50.0 parts |
| Calcium hydrogen phosphate | 70.0 parts |
| Lactose | 40.0 parts |
| Corn starch | 35.0 parts |
| Polyvinylpyrrolidone | 3.5 parts |
| Magnesium stearate | 1.5 parts |
| Total | 200.0 parts |

PREPARATION

The active ingredient, the calcium acid phosphate, the lactose and the corn starch are intimately admixed, and the mixture is homogeneously moistened with an aqueous solution of the polyvinylpyrrolidone. Then the moist mass is granulated through a 2 mm-mesh screen, dried at 50° C in a circulating air drier, and again passed through a 1.5 mm-mesh screen. After adding the magnesium stearate the composition is compressed into 200 mgm-tablets, each of which contains 50 mgm of the active ingredient and is an oral dosage unit composition.

EXAMPLE 60

Coated pills

The pill core composition is compounded from the following ingredients:

| | |
|---|---|
| N-[1-Ethyl-pyrrolidyl-(2)-methyl]-2-amino-5-chloro-3-trifluoromethyl-benzoic acid amide hydrochloride | 20.0 parts |
| Calcium acid phosphate | 35.0 parts |
| Lactose | 16.8 parts |
| Corn starch | 16.0 parts |
| Polyvinylpyrrolidone | 1.5 parts |
| Magnesium stearate | 0.7 parts |
| Total | 90.0 parts |

PREPARATION

The ingredients are compounded in the same manner as in the preceding example, and the composition is compressed into 90 mgm-pill cores which are then coated with a thin shell consisting essentially of talcum and sugar, and finally polished with beeswax. Each coated pill contains 20 mgm of the active ingredient and is an oral dosage unit composition.

EXAMPLE 61

Gelatin capsules

The capsule filler composition is compounded from the following ingredients:

| | |
|---|---|
| N-[1-Ethyl-pyrrolidyl-(2)-methyl]-2-amino-5-chloro-3-trifluoromethyl-benzoic acid amide hydrochloride | 25.0 parts |
| Dried corn starch | 72.0 parts |
| Pulverized lactose | 50.0 parts |
| Magnesium stearate | 3.0 parts |
| Total | 150.0 parts |

PREPARATION

The active ingredient and the inert excipients are passed through a 0.75 mm-mesh screen, then intimately admixed with each other, and 150 mgm-portions of the mixture are filled into No. 4 hard gelatin capsules. Each capsule contains 25 mgm of the active ingredient and is an oral dosage unit composition.

EXAMPLE 62

Solution

The solution is compounded from the following ingredients:

| | | |
|---|---|---|
| N-[1-Ethyl-pyrrolidyl-(2)-methyl]-2-amino-5-chloro-3-trifluoromethyl-benzoic acid amide hydrochloride | 0.1667 | parts |
| Carboxymethyl cellulose | 0.1 | parts |
| Methyl p-hydroxybenzoate | 0.05 | parts |
| Propyl p-hydroxybenzoate | 0.01 | parts |
| Cane sugar | 10.0 | parts |
| Glycerin | 5.0 | parts |
| Aqueous 70% sorbitol solution | 20.0 | parts |
| Flavoring | 0.3 | parts |
| Distilled water q.s.ad | 100.0 | parts by vol. |

PREPARATION

The distilled water is heated to 70° C, and the benzoates as well as the glycerin and carboxymethyl cellulose are dissolved therein. The solution is cooled to room temperature, the active ingredient is added, and the mixture is stirred until the active ingredient dissolves. After adding and dissolving the sugar, the sorbitol solution and the flavoring, the air is removed from the solution by stirring in vacuo. 15 ml (1 tablespoon) of the solution contain 25 mgm of the active ingredient and are an oral dosage unit composition.

EXAMPLE 63

Hypodermic solution

The solution is compounded from the following ingredients:

| | | |
|---|---|---|
| N[1-Ethyl-pyrrolidyl-(2)-methyl]-2-amino-5-chloro-3-trifluoromethyl-benzoic acid amide hydrochloride | 10.0 | parts |
| Citric acid | 1.0 | parts |
| $Na_2HPO_4 \cdot 2 H_2O$ | 3.5 | parts |
| Sodium chloride | 6.5 | parts |
| Distilled water q.s.ad | 1000.0 | parts by vol. |

PREPARATION

The major amount of the required distilled water, saturated with $N_2$, is placed into a graduated vessel made of inert material, and the buffers, the active ingredient and the sodium chloride are dissolved therein, while stirring and continually introducing nitrogen. The solution is then diluted to the indicated volume with the remaining $N_2$-saturated distilled water and finally filtered through a membrane filter until sterile. The filtrate is filled into clean, sterilized brown 1 ml ampules in a nitrogen gas atmosphere. Each ampule contains 10 mgm of the active ingredient, and the contents thereof are an injectable solution.

EXAMPLE 64

Rectal suppositories

The suppository composition is compounded from the following ingredients:

| | |
|---|---|
| N-[1-Ethyl-pyrrolidyl-(2)-methyl]-2-amino-5-chloro-3-trifluoromethyl-benzoic acid amide hydrochloride | 0.050 parts |
| Suppository base (e.g. cocoa butter) | 1.650 parts |
| Total | 1.700 parts |

PREPARATION

The suppository base is melted and cooled to 40° C, and the milled active ingredient is added thereto and homogeneously blended in. 1.7 gm-portions of the resulting composition are poured into cooled suppository molds and allowed to harden therein. Each suppository contains 50 mgm of the active ingredient and is a rectal dosage unit composition.

Any of the other compounds of the present invention may be substituted for the particular amino-benzoic acid amide salt in illustrative Examples 59 to 64. Likewise, the amount of active ingredient in these examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

Note: Whenever the expression "pyrrolidyl" or "pyrrolidinyl" is used as a substituent, the fully hydrogenated, five-membered heterocycle of the formula

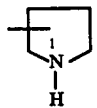

is to be understood

We claim:

1. A compound of the formula

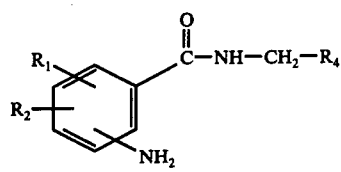

wherein
 $R_1$ is hydrogen, chlorine or bromine,
 $R_2$ is methyl, fluorine, chlorine, bromine, trifluoromethyl or nitro, and
 $R_4$ is 1-(alkyl of 1 to 3 carbon atoms)-pyrrolidinyl (2), or a non-toxic, phamacologically acceptable acid addition salt thereof.

2. A compound of claim 1, where
 the $-NH_2$ substituent is in the o— or p— position with respect to the carbonyl group,
 substitnents $R_1$ and $R_2$ are in the 3- and 5- position, respectively, in relation to the carbonyl group,
 one of $R_1$ and $R_2$ is hydrogen, chlorine or bromine,
 the other of $R_1$ and $R_2$ is methyl, flourine, chlorine, bromine, trifluoromethyl or nitro, and
 $R_4$ is 1-(alkyl of 1 to 2 carbon atoms)-pyrrolidinyl-(2), or a non-toxic, pharmacologically acceptable acid addition salt thereof.

3. A compound of claim 2, where
 $R_1$ is hydrogen, chlorine or bromine,
 $R_2$ is trifluoromethyl or nitro, and
 $R_4$ is 1-ethyl-pyrrolidinyl-(2),
 or a non-toxic, pharmacologically acceptable acid addition salt thereof.

4. A compound of claim 3, which is N-[1-ethylpyrrolidinyl-(2)-methyl]-2-amino-5-chloro-3-trifluoromethylbenzoic acid amide or a non-toxic, pharmacologically acceptable acid addition salt thereof.

5. A compound of claim 3, which is N-[1-ethylpyrrolidinyl-(2)-methyl]-4-amino-3-chloro-5-trifluoromethylbenzoic acid amide or a non-toxic, pharmacologically acceptable acid addition salt thereof.

6. An anxiolytic or anticonvulsive pharmaceutical dosage unit composition consisting essentially of an inert pharmaceutical carrier and an effective amount of a compound of claim 1.

7. The method of relieving anxiety and convulsions in a warm-blooded animal in need thereof, which comprises perorally, parenterally or rectally administering to said animal an effective anxiolytic or anticonvulsive amount of a compound of claim 1.

* * * * *

UNITED STATES PATENT OFFICE
CERTIFICATE OF CORRECTION

Patent No. 4,093,734          Dated June 6, 1978

Inventor(s) GERD KRÜGER, JOHANNES KECK, KLAUS REINHOLD NOLL, HELMUT PIEPER, HARALD ZIEGLER, HELMUT BALLHAUSE and JOACHIM KÄHLING It is certified that error appears in the above-identified patent and that said Letters Patent are hereby corrected as shown below:

Col. 4, line 1, correct the line by inserting after "halogenating" the word --agent--.

Col. 6, line 60, correct the heading "EXAMPLE 14" to read --EXAMPLE 4--.

Col. 9, line 50, correct "C]m.p." to read --C[m.p.--

Col. 15, between lines 60 and 65, third line under the caption "DIFFERENCE" correct "°3.9+" to --+3.9+--

Col. 16, line 6, correct "p>0.05" to read --p <0.05-- line 7, correct "p >0.1" to read --p <0.1--

Signed and Sealed this

Fifth Day of December 1978

[SEAL]

Attest:

RUTH C. MASON
Attesting Officer

DONALD W. BANNER
Commissioner of Patents and Trademarks